United States Patent [19]

Alborn, Jr. et al.

[11] Patent Number: 5,587,307
[45] Date of Patent: Dec. 24, 1996

[54] **FEMA GENE OF *STAPHYLOCOCCUS EPIDERMIDIS*, FEMA PROTEIN, AND VECTORS AND MICROORGANISMS COMPRISING THE FEMA GENE**

[75] Inventors: William E. Alborn, Jr., Carmel; JoAnn Hoskins, Indianapolis; Paul L. Skatrud, Greenwood, all of Ind.; Serhat Ünal, Ankara, Turkey

[73] Assignee: Eli Lilly and Company, Indianapolis, Ind.

[21] Appl. No.: 330,154

[22] Filed: Oct. 27, 1994

Related U.S. Application Data

[63] Continuation of Ser. No. 208,925, Mar. 9, 1994, abandoned, which is a continuation of Ser. No. 57,163, Apr. 30, 1993, abandoned.

[51] Int. Cl.$^6$ .......................... C12N 15/31; C12N 15/70; C07K 14/31
[52] U.S. Cl. ..................... 435/240.1; 530/350; 536/23.7; 435/240.2; 435/240.4; 435/252.3
[58] Field of Search .......................... 530/350; 435/69.1, 435/320.1, 252.3, 240.1, 240.2, 240.4, 252.31, 252.32, 252.33, 252.34, 252.35; 536/23.7

[56] References Cited

PUBLICATIONS

Tesch et al., *Antimicrobial Agents & Chemotherapy*, vol. 32(10):1494–1499, Oct. 1988.
Unal et al., *J. Clin. Microb.*, vol. 30, No. 7, pp. 1685–1691, Jul. 1992.
Sambrook et al., *Molecular Cloning: A Laboratory Manual*, Cold Spring Harbor Press, 1989, pp. 11.3–11.19.
Kornblum et al., *Eur. J. Clin. Microbiol.* (1986) 5:714–718.
Berger–Bächi et al., *Antimicrob. Agents Chemother.* (1992) 36:1367–1373.
Maidhof et al., *J. Bacteriol.* (1991) 173:3507–3513.
Murakami and Tomasz, *J. Bacteriol.* (1989) 171:874–879.
Berger–Bächi et al., *Mol. Gen. Genet.* (1989) 219:263–269.

*Primary Examiner*—Keith D. Hendricks
*Attorney, Agent, or Firm*—Amy E. Hamilton

[57] ABSTRACT

The instant invention provides the femA gene of *Staphylococcus epidermidis* and all degenerate sequences thereof, the protein encoded by the femA gene (FemA), and vectors and microorganisms comprising genes encoding the FemA protein.

5 Claims, 2 Drawing Sheets

FEMA GENE OF *STAPHYLOCOCCUS EPIDERMIDIS*, FEMA PROTEIN, AND VECTORS AND MICROORGANISMS COMPRISING THE FEMA GENE

This application is a continuation of application Ser. No. 08/208,925, filed Mar. 9, 1994 now abandoned, which is a continuation of Ser. No. 08/057,163 filed Apr. 30, 1993, now abandoned.

BACKGROUND OF THE INVENTION

Clinical isolates of staphylococci (*Staphylococcus aureus* and *S. epidermidis*) which cause serious infections due to their intrinsic resistance to beta-lactamase-stable beta-lactam antibiotics (e.g., methicillin) carry the mecA gene. Song et al., *FEBS Lett.* 221:167–171 (1987). This gene encodes a putative cell wall biosynthetic enzyme referred to as penicillin binding protein 2a (PBP2a). PBP2a, which binds beta-lactams only at concentrations well above therapeutic efficacy, apparently can functionally substitute for all the staphylococcal PBPs and permit growth when the host organism is threatened by beta-lactams. Hartman and Tomasz, *J. Bacteriol.* 158:513–516 (1984). Wu et al., *Antimicrob. Agents Chemother.* 36:533–539 (1992) and Ryffel et al., *Gene* 94:137–138 (1990).

The mecA gene is not a normal part of the staphylococcal genome. The organism which donated mecA to the staphylococci remains unidentified. Despite the uniform presence of mecA in methicillin-resistant clinical isolates, these isolates vary considerably in their degree of resistance to methicillin. This variation in phenotypic expression within a population has been referred to as heterogenous expression. Matthews and Stewart, *FEMS Microbiol. Lett.* 22:161–166 (1984). Typically, most cells exhibit low-level resistance to methicillin and only a minority of the population express high-level resistance, perhaps only one in $10^8$ cells. Tomasz et al., *Antimicrob. Agents Chemother.* 35:124–129 (1991). Although expression of methicillin resistance is dependent upon the presence of PBP2a, it appears to be somewhat independent of the amount of PBP2a, suggesting important roles for other factors. Chambers and Hackbarth, *Antimicrob. Agents Chemother.* 31:1982–1988 (1987) and Murakami and Tomasz, *J. Bacteriol.* 171:874–879 (1989).

Tn551 insertional mutagenesis of methicillin-resistant *S. aureus* revealed numerous sites which influence the level of methicillin resistance but are non linked to mecA and do not perturb the expression of PBP2a. Berger-Bächi et al., *Antimicrob. Agents Chemother.* 36:1367–1373 (1992); Kornblum et al., *Eur. J. Clin. Microbiol.* 5:714–718 (1986); Berger-Bächi et al., *Mol. Gen. Genet.* 219:263–269 (1989) and Maidhof et al., *J. Bacteriol.* 173:3507–3513 (1991). Those factors described thus far generally depress the MIC of beta-lactam resistant strains. Some of the genetic loci which demonstrate such an effect on methicillin resistance were designated factors essential for methicillin resistance (fem). Berger-Bächi et al., *Mol. Gen. Genet.* 219:263–269 (1989). In contrast to mecA, the genes which encode influential factors are probably present in both resistant and susceptible strains of *S. aureus* and *S. epidermidis*. Information obtained from gene disruption studies of femA and femB in *S. aureus* indicated that in addition to enhanced sensitivity to methicillin, homogeneously methicillin-resistant *S. aureus* strains carrying such gene disruptions have a reduced glycine content in the peptidoglycan component of their cell walls (Maidhof et al., *J. Bacteriol.* 173:3507–3513 (1991)) and exhibit reduced rates of cell wall turnover and autolysis (de Jonge et al., *J. Bacteriol.* 173:1105–1110 (1991)).

Genetic factors, other than mecA, that influence the expression of methicillin resistance in *S. epidermidis* have, until now, not been described at the molecular level. The present invention provides DNA sequences encoding the FemA protein of *Staphylococcus epidermidis*, the FemA protein itself, and vectors and microorganisms comprising the femA gene of *S. epidermidis*.

SUMMARY OF THE INVENTION

The present invention provides DNA sequences encoding the FemA protein of *Staphylococcus epidermidis*, including the natural gene sequence designated femA (SEQ ID NO:1). Thus, included in the present invention is any DNA compound that comprises an isolated DNA sequence encoding SEQ ID NO:2. SEQ ID NO:2 is as follows:

| Met 1 | Lys | Met | Lys | Phe 5 | Thr | Asn | Leu | Thr | Ala 10 | Lys | Glu | Phe | Ser | Asp 15 | Phe |
|---|---|---|---|---|---|---|---|---|---|---|---|---|---|---|---|
| Thr | Asp | Arg | Met 20 | Thr | Tyr | Ser | His | Phe 25 | Thr | Gln | Met | Glu | Gly 30 | Asn | Tyr |
| Glu | Leu | Lys 35 | Val | Ala | Glu | Gly | Thr 40 | Glu | Ser | His | Leu | Val 45 | Gly | Ile | Lys |
| Asn | Asn 50 | Asp | Asn | Glu | Val | Ile 55 | Ala | Ala | Cys | Leu | Leu 60 | Thr | Ala | Val | Pro |
| Val 65 | Met | Lys | Ile | Phe | Lys 70 | Tyr | Phe | Tyr | Ser | Asn 75 | Arg | Gly | Pro | Val | Ile 80 |
| Asp | Tyr | Asn | Asn | Lys 85 | Glu | Leu | Val | His | Phe 90 | Phe | Phe | Asn | Glu | Leu 95 | Ser |
| Lys | Tyr | Val | Lys 100 | Lys | Tyr | Asn | Cys | Leu 105 | Tyr | Leu | Arg | Val | Asp 110 | Pro | Tyr |
| Leu | Pro | Tyr 115 | Gln | Tyr | Leu | Asn | His 120 | Glu | Gly | Glu | Ile | Thr 125 | Gly | Asn | Ala |
| Gly | His 130 | Asp | Trp | Ile | Phe | Asp 135 | Glu | Leu | Glu | Ser | Leu 140 | Gly | Tyr | Lys | His |
| Glu 145 | Gly | Phe | His | Lys | Gly 150 | Phe | Asp | Pro | Val | Leu 155 | Gln | Ile | Arg | Tyr | His 160 |

| | | | | | | | | | | | | | | |
|---|---|---|---|---|---|---|---|---|---|---|---|---|---|---|
| Ser | Val | Leu | Asn | Leu 165 | Ala | Asn | Lys | Ser | Ala 170 | Asn | Asp | Val | Leu | Lys 175 | Asn |
| Met | Asp | Gly | Leu 180 | Arg | Lys | Arg | Asn | Thr 185 | Lys | Lys | Val | Lys | Lys 190 | Asn | Gly |
| Val | Lys | Val 195 | Arg | Phe | Leu | Ser | Glu 200 | Glu | Glu | Leu | Pro | Ile 205 | Phe | Arg | Ser |
| Phe | Met 210 | Glu | Asp | Thr | Ser | Glu 215 | Thr | Lys | Asp | Phe | Ala 220 | Asp | Arg | Glu | Asp |
| Ser 225 | Phe | Tyr | Tyr | Asn | Arg 230 | Phe | Lys | His | Tyr | Lys 235 | Asp | Arg | Val | Leu | Val 240 |
| Pro | Leu | Ala | Tyr | Ile 245 | Asn | Phe | Asp | Glu | Tyr 250 | Ile | Glu | Glu | Leu | Asn 255 | Asn |
| Glu | Arg | Asn | Val 260 | Leu | Asn | Lys | Asp | Tyr 265 | Asn | Lys | Ala | Leu | Lys 270 | Asp | Ile |
| Glu | Lys | Arg 275 | Pro | Glu | Asn | Lys | Lys 280 | Ala | His | Asn | Lys | Lys 285 | Glu | Asn | Leu |
| Glu | Gln 290 | Gln | Leu | Asp | Ala | Asn 295 | Gln | Gln | Lys | Ile | Asn 300 | Glu | Ala | Lys | Asn |
| Leu 305 | Lys | Gln | Glu | His | Gly 310 | Asn | Glu | Leu | Pro | Ile 315 | Ser | Ala | Gly | Phe | Phe 320 |
| Ile | Ile | Asn | Pro | Phe 325 | Glu | Val | Val | Tyr | Tyr 330 | Ala | Gly | Gly | Thr | Ser 335 | Asn |
| Arg | Tyr | Arg | His 340 | Phe | Ala | Gly | Ser | Tyr 345 | Ala | Val | Gln | Trp | Lys 350 | Met | Ile |
| Asn | Tyr | Ala 355 | Ile | Glu | His | Gly | Ile 360 | Asn | Arg | Tyr | Asn | Phe 365 | Tyr | Gly | Ile |
| Ser | Gly 370 | Asp | Phe | Ser | Glu | Asp 375 | Ala | Glu | Asp | Ala | Gly 380 | Val | Val | Lys | Phe |
| Lys 385 | Lys | Gly | Tyr | Asp | Ala 390 | Asp | Val | Ile | Glu | Tyr 395 | Val | Gly | Asp | Phe | Ile 400 |
| Lys | Pro | Ile | Asn | Lys 405 | Pro | Met | Tyr | Asn | Ile 410 | Tyr | Arg | Thr | Leu | Lys 415 | Lys |
| Leu | Lys | Lys | | | | | | | | | | | | | |

The natural femA sequence is encompassed by the present invention as a DNA compound which comprises the isolated DNA sequence which is SEQ ID NO:1. SEQ ID NO:1 is as follows:

```
ATG AAG ATG AAG TTT ACG AAT TTG ACA GCT AAA GAA TTT AGT GAC TTT    48
Met Lys Met Lys Phe Thr Asn Leu Thr Ala Lys Glu Phe Ser Asp Phe
 1           5                  10                  15

ACT GAT CGT ATG ACA TAT AGT CAT TTT ACA CAA ATG GAA GGT AAT TAC    96
Thr Asp Arg Met Thr Tyr Ser His Phe Thr Gln Met Glu Gly Asn Tyr
             20                  25                  30

GAA TTA AAG GTT GCT GAA GGT ACC GAG TCA CAT TTA GTT GGA ATT AAA   144
Glu Leu Lys Val Ala Glu Gly Thr Glu Ser His Leu Val Gly Ile Lys
         35                  40                  45

AAT AAT GAT AAC GAA GTG ATT GCA GCT TGT TTA TTA ACA GCT GTT CCT   192
Asn Asn Asp Asn Glu Val Ile Ala Ala Cys Leu Leu Thr Ala Val Pro
     50                  55                  60

GTA ATG AAA ATA TTT AAA TAT TTT TAT TCC AAT CGC GGT CCA GTA ATA   240
Val Met Lys Ile Phe Lys Tyr Phe Tyr Ser Asn Arg Gly Pro Val Ile
 65                  70                  75                  80

GAT TAT AAT AAT AAA GAG CTT GTA CAT TTT TTC TTT AAT GAA TTG AGT   288
Asp Tyr Asn Asn Lys Glu Leu Val His Phe Phe Phe Asn Glu Leu Ser
                 85                  90                  95
```

-continued

| | | | | | | | | | | | | | | | | |
|---|---|---|---|---|---|---|---|---|---|---|---|---|---|---|---|---|
| AAA | TAT | GTA | AAA | AAA | TAT | AAT | TGT | TTA | TAT | TTA | AGA | GTT | GAC | CCA | TAC | 336 |
| Lys | Tyr | Val | Lys | Lys | Tyr | Asn | Cys | Leu | Tyr | Leu | Arg | Val | Asp | Pro | Tyr | |
| | | 100 | | | | | 105 | | | | | 110 | | | | |
| CTT | CCA | TAT | CAA | TAT | TTA | AAT | CAT | GAG | GGA | GAA | ATA | ACT | GGA | AAT | GCA | 384 |
| Leu | Pro | Tyr | Gln | Tyr | Leu | Asn | His | Glu | Gly | Glu | Ile | Thr | Gly | Asn | Ala | |
| | | 115 | | | | | 120 | | | | | 125 | | | | |
| GGT | CAT | GAT | TGG | ATT | TTT | GAT | GAA | TTA | GAG | AGT | TTA | GGA | TAT | AAA | CAC | 432 |
| Gly | His | Asp | Trp | Ile | Phe | Asp | Glu | Leu | Glu | Ser | Leu | Gly | Tyr | Lys | His | |
| | 130 | | | | | 135 | | | | | 140 | | | | | |
| GAA | GGA | TTC | CAC | AAA | GGA | TTT | GAT | CCT | GTA | TTA | CAA | ATC | CGA | TAT | CAT | 480 |
| Glu | Gly | Phe | His | Lys | Gly | Phe | Asp | Pro | Val | Leu | Gln | Ile | Arg | Tyr | His | |
| 145 | | | | | 150 | | | | | 155 | | | | | 160 | |
| TCT | GTT | CTA | AAT | TTA | GCA | AAC | AAA | AGT | GCT | AAT | GAT | GTT | TTA | AAA | AAC | 528 |
| Ser | Val | Leu | Asn | Leu | Ala | Asn | Lys | Ser | Ala | Asn | Asp | Val | Leu | Lys | Asn | |
| | | | 165 | | | | | 170 | | | | | 175 | | | |
| ATG | GAT | GGT | TTA | AGA | AAG | CGT | AAT | ACT | AAA | AAA | GTT | AAG | AAA | AAT | GGA | 576 |
| Met | Asp | Gly | Leu | Arg | Lys | Arg | Asn | Thr | Lys | Lys | Val | Lys | Lys | Asn | Gly | |
| | | | 180 | | | | | 185 | | | | | 190 | | | |
| GTT | AAA | GTC | CGC | TTT | TTA | TCT | GAA | GAA | GAG | TTA | CCT | ATA | TTT | AGG | TCA | 624 |
| Val | Lys | Val | Arg | Phe | Leu | Ser | Glu | Glu | Glu | Leu | Pro | Ile | Phe | Arg | Ser | |
| | | 195 | | | | | 200 | | | | | 205 | | | | |
| TTT | ATG | GAG | GAT | ACC | TCT | GAA | ACT | AAA | GAT | TTT | GCA | GAT | AGA | GAA | GAT | 672 |
| Phe | Met | Glu | Asp | Thr | Ser | Glu | Thr | Lys | Asp | Phe | Ala | Asp | Arg | Glu | Asp | |
| | 210 | | | | | 215 | | | | | 220 | | | | | |
| AGT | TTT | TAT | TAC | AAC | AGA | TTC | AAA | CAT | TAT | AAA | GAC | CGT | GTT | TTA | GTA | 720 |
| Ser | Phe | Tyr | Tyr | Asn | Arg | Phe | Lys | His | Tyr | Lys | Asp | Arg | Val | Leu | Val | |
| 225 | | | | | 230 | | | | | 235 | | | | | 240 | |
| CCA | CTA | GCC | TAT | ATT | AAC | TTT | GAT | GAG | TAT | ATA | GAG | GAA | CTA | AAT | AAT | 768 |
| Pro | Leu | Ala | Tyr | Ile | Asn | Phe | Asp | Glu | Tyr | Ile | Glu | Glu | Leu | Asn | Asn | |
| | | | 245 | | | | | 250 | | | | | 255 | | | |
| GAA | AGA | AAT | GTG | CTT | AAT | AAA | GAT | TAT | AAT | AAA | GCT | TTA | AAA | GAC | ATT | 816 |
| Glu | Arg | Asn | Val | Leu | Asn | Lys | Asp | Tyr | Asn | Lys | Ala | Leu | Lys | Asp | Ile | |
| | | | 260 | | | | | 265 | | | | | 270 | | | |
| GAG | AAA | CGT | CCA | GAG | AAT | AAA | AAA | GCA | CAT | AAC | AAA | AAG | GAA | AAT | TTA | 864 |
| Glu | Lys | Arg | Pro | Glu | Asn | Lys | Lys | Ala | His | Asn | Lys | Lys | Glu | Asn | Leu | |
| | | 275 | | | | | 280 | | | | | 285 | | | | |
| GAA | CAA | CAA | CTC | GAT | GCA | AAT | CAG | CAA | AAA | ATT | AAT | GAA | GCT | AAA | AAC | 912 |
| Glu | Gln | Gln | Leu | Asp | Ala | Asn | Gln | Gln | Lys | Ile | Asn | Glu | Ala | Lys | Asn | |
| | 290 | | | | | 295 | | | | | 300 | | | | | |
| TTA | AAA | CAA | GAA | CAT | GGC | AAT | GAA | TTA | CCC | ATC | TCT | GCT | GGC | TTC | TTT | 960 |
| Leu | Lys | Gln | Glu | His | Gly | Asn | Glu | Leu | Pro | Ile | Ser | Ala | Gly | Phe | Phe | |
| 305 | | | | | 310 | | | | | 315 | | | | | 320 | |
| ATA | ATT | AAT | CCG | TTT | GAA | GTA | GTT | TAC | TAC | GCT | GGT | GGA | ACT | TCA | AAT | 1008 |
| Ile | Ile | Asn | Pro | Phe | Glu | Val | Val | Tyr | Tyr | Ala | Gly | Gly | Thr | Ser | Asn | |
| | | | 325 | | | | | 330 | | | | | 335 | | | |
| CGT | TAT | CGC | CAT | TTT | GCA | GGG | AGC | TAT | GCG | GTT | CAA | TGG | AAG | ATG | ATT | 1056 |
| Arg | Tyr | Arg | His | Phe | Ala | Gly | Ser | Tyr | Ala | Val | Gln | Trp | Lys | Met | Ile | |
| | | 340 | | | | | 345 | | | | | 350 | | | | |
| AAC | TAT | GCA | ATT | GAA | CAT | GGT | ATT | AAT | CGG | TAT | AAT | TTC | TAT | GGT | ATT | 1104 |
| Asn | Tyr | Ala | Ile | Glu | His | Gly | Ile | Asn | Arg | Tyr | Asn | Phe | Tyr | Gly | Ile | |
| | | 355 | | | | | 360 | | | | | 365 | | | | |
| AGT | GGT | GAC | TTT | AGT | GAA | GAT | GCT | GAA | GAT | GCT | GGC | GTA | GTT | AAG | TTT | 1152 |
| Ser | Gly | Asp | Phe | Ser | Glu | Asp | Ala | Glu | Asp | Ala | Gly | Val | Val | Lys | Phe | |
| | 370 | | | | | 375 | | | | | 380 | | | | | |
| AAA | AAG | GGC | TAT | GAT | GCC | GAT | GTT | ATA | GAA | TAC | GTT | GGT | GAC | TTT | ATT | 1200 |
| Lys | Lys | Gly | Tyr | Asp | Ala | Asp | Val | Ile | Glu | Tyr | Val | Gly | Asp | Phe | Ile | |
| 385 | | | | | 390 | | | | | 395 | | | | | 400 | |
| AAA | CCT | ATT | AAT | AAA | CCA | ATG | TAT | AAC | ATT | TAT | AGA | ACA | CTT | AAA | AAA | 1248 |
| Lys | Pro | Ile | Asn | Lys | Pro | Met | Tyr | Asn | Ile | Tyr | Arg | Thr | Leu | Lys | Lys | |
| | | | 405 | | | | | 410 | | | | | 415 | | | |
| CTA | AAG | AAA | | | | | | | | | | | | | | 1257 |
| Leu | Lys | Lys | | | | | | | | | | | | | | |

The present invention also includes the protein encoded by SEQ ID NO: 1 in purified form. Also included are recombinant DNA vectors, including expression vectors, that comprise DNA sequences encoding FemA.

BRIEF DESCRIPTION OF THE FIGURES

The restriction site and function maps presented in the accompanying drawings are approximate representations of the recombinant DNA vectors discussed herein, The restriction site information is not exhaustive; therefore, there may be more restriction sites of a given type on the vector than actually shown on the map.

DETAILED DESCRIPTION OF THE INVENTION

The instant invention provides the femA gene of *Staphylococcus epidermidis* and all degenerate sequences thereof, the protein encoded by the femA gene (FemA), and vectors and microorganisms comprising genes encoding the FemA protein. In the practice of the invention as exemplified herein, the FemA protein comprises the amino acid sequence, which is SEQ ID NO 2:

| Met 1 | Lys | Met | Lys | Phe 5 | Thr | Asn | Leu | Thr | Ala 10 | Lys | Glu | Phe | Ser | Asp 15 | Phe |
| Thr | Asp | Arg | Met 20 | Thr | Tyr | Ser | His | Phe 25 | Thr | Gln | Met | Glu | Gly 30 | Asn | Tyr |
| Glu | Leu | Lys 35 | Val | Ala | Glu | Gly | Thr 40 | Glu | Ser | His | Leu | Val 45 | Gly | Ile | Lys |
| Asn | Asn 50 | Asp | Asn | Glu | Val | Ile 55 | Ala | Ala | Cys | Leu | Leu 60 | Thr | Ala | Val | Pro |
| Val 65 | Met | Lys | Ile | Phe | Lys 70 | Tyr | Phe | Tyr | Ser | Asn 75 | Arg | Gly | Pro | Val | Ile 80 |
| Asp | Tyr | Asn | Asn | Lys 85 | Glu | Leu | Val | His | Phe 90 | Phe | Phe | Asn | Glu | Leu 95 | Ser |
| Lys | Tyr | Val | Lys 100 | Lys | Tyr | Asn | Cys | Leu 105 | Tyr | Leu | Arg | Val | Asp 110 | Pro | Tyr |
| Leu | Pro | Tyr 115 | Gln | Tyr | Leu | Asn | His 120 | Glu | Gly | Glu | Ile | Thr 125 | Gly | Asn | Ala |
| Gly | His 130 | Asp | Trp | Ile | Phe | Asp 135 | Glu | Leu | Glu | Ser | Leu 140 | Gly | Tyr | Lys | His |
| Glu 145 | Gly | Phe | His | Lys | Gly 150 | Phe | Asp | Pro | Val | Leu 155 | Gln | Ile | Arg | Tyr | His 160 |
| Ser | Val | Leu | Asn | Leu 165 | Ala | Asn | Lys | Ser | Ala 170 | Asn | Asp | Val | Leu | Lys 175 | Asn |
| Met | Asp | Gly | Leu 180 | Arg | Lys | Arg | Asn | Thr 185 | Lys | Lys | Val | Lys | Lys 190 | Asn | Gly |
| Val | Lys | Val 195 | Arg | Phe | Leu | Ser | Glu 200 | Glu | Leu | Pro | Ile 205 | Phe | Arg | Ser |
| Phe | Met 210 | Glu | Asp | Thr | Ser | Glu 215 | Thr | Lys | Asp | Phe | Ala 220 | Asp | Arg | Glu | Asp |
| Ser 225 | Phe | Tyr | Tyr | Asn | Arg 230 | Phe | Lys | His | Tyr | Lys 235 | Asp | Arg | Val | Leu | Val 240 |
| Pro | Leu | Ala | Tyr | Ile 245 | Asn | Phe | Asp | Glu | Tyr 250 | Ile | Glu | Glu | Leu | Asn 255 | Asn |
| Glu | Arg | Asn | Val 260 | Leu | Asn | Lys | Asp | Tyr 265 | Asn | Lys | Ala | Leu | Lys 270 | Asp | Ile |
| Glu | Lys | Arg 275 | Pro | Glu | Asn | Lys | Lys 280 | Ala | His | Asn | Lys | Lys 285 | Glu | Asn | Leu |
| Glu | Gln 290 | Gln | Leu | Asp | Ala | Asn 295 | Gln | Gln | Lys | Ile | Asn 300 | Glu | Ala | Lys | Asn |
| Leu 305 | Lys | Gln | Glu | His | Gly 310 | Asn | Glu | Leu | Pro | Ile 315 | Ser | Ala | Gly | Phe | Phe 320 |
| Ile | Ile | Asn | Pro | Phe 325 | Glu | Val | Val | Tyr | Tyr 330 | Ala | Gly | Gly | Thr | Ser 335 | Asn |
| Arg | Tyr | Arg | His 340 | Phe | Ala | Gly | Ser | Tyr 345 | Ala | Val | Gln | Trp | Lys 350 | Met | Ile |

-continued

| | | | | | | | | | | | | | | |
|---|---|---|---|---|---|---|---|---|---|---|---|---|---|---|
| Asn | Tyr | Ala | Ile<br>355 | Glu | His | Gly | Ile<br>360 | Asn | Arg | Tyr | Asn | Phe<br>365 | Tyr | Gly | Ile |

| | | | | | | | | | | | | |
|---|---|---|---|---|---|---|---|---|---|---|---|---|
| Ser | Gly<br>370 | Asp | Phe | Ser | Glu | Asp<br>375 | Ala | Glu | Asp | Ala | Gly<br>380 | Val | Val | Lys | Phe |

Lys Lys Gly Tyr Asp Ala Asp Val Ile Glu Tyr Val Gly Asp Phe Ile
385                390                 395                400

Lys Pro Ile Asn Lys Pro Met Tyr Asn Ile Tyr Arg Thr Leu Lys Lys
               405                410                      415

Leu Lys Lys

The present invention also provides the natural femA gene found in *Staphylococcus epidermidis*, embodied in SEQ ID NO: 1:

```
ATG AAG ATG AAG TTT ACG AAT TTG ACA GCT AAA GAA TTT AGT GAC TTT   48
Met Lys Met Lys Phe Thr Asn Leu Thr Ala Lys Glu Phe Ser Asp Phe
1             5                   10                  15

ACT GAT CGT ATG ACA TAT AGT CAT TTT ACA CAA ATG GAA GGT AAT TAC   96
Thr Asp Arg Met Thr Tyr Ser His Phe Thr Gln Met Glu Gly Asn Tyr
            20                  25                  30

GAA TTA AAG GTT GCT GAA GGT ACC GAG TCA CAT TTA GTT GGA ATT AAA  144
Glu Leu Lys Val Ala Glu Gly Thr Glu Ser His Leu Val Gly Ile Lys
        35                  40                  45

AAT AAT GAT AAC GAA GTG ATT GCA GCT TGT TTA TTA ACA GCT GTT CCT  192
Asn Asn Asp Asn Glu Val Ile Ala Ala Cys Leu Leu Thr Ala Val Pro
    50                  55                  60

GTA ATG AAA ATA TTT AAA TAT TTT TAT TCC AAT CGC GGT CCA GTA ATA  240
Val Met Lys Ile Phe Lys Tyr Phe Tyr Ser Asn Arg Gly Pro Val Ile
65              70                  75                  80

GAT TAT AAT AAT AAA GAG CTT GTA CAT TTT TTC TTT AAT GAA TTG AGT  288
Asp Tyr Asn Asn Lys Glu Leu Val His Phe Phe Phe Asn Glu Leu Ser
                85                  90                  95

AAA TAT GTA AAA AAA TAT AAT TGT TTA TAT TTA AGA GTT GAC CCA TAC  336
Lys Tyr Val Lys Lys Tyr Asn Cys Leu Tyr Leu Arg Val Asp Pro Tyr
            100                 105                 110

CTT CCA TAT CAA TAT TTA AAT CAT GAG GGA GAA ATA ACT GGA AAT GCA  384
Leu Pro Tyr Gln Tyr Leu Asn His Glu Gly Glu Ile Thr Gly Asn Ala
        115                 120                 125

GGT CAT GAT TGG ATT TTT GAT GAA TTA GAG AGT TTA GGA TAT AAA CAC  432
Gly His Asp Trp Ile Phe Asp Glu Leu Glu Ser Leu Gly Tyr Lys His
    130                 135                 140

GAA GGA TTC CAC AAA GGA TTT GAT CCT GTA TTA CAA ATC CGA TAT CAT  480
Glu Gly Phe His Lys Gly Phe Asp Pro Val Leu Gln Ile Arg Tyr His
145                 150                 155                 160

TCT GTT CTA AAT TTA GCA AAC AAA AGT GCT AAT GAT GTT TTA AAA AAC  528
Ser Val Leu Asn Leu Ala Asn Lys Ser Ala Asn Asp Val Leu Lys Asn
                165                 170                 175

ATG GAT GGT TTA AGA AAG CGT AAT ACT AAA AAA GTT AAG AAA AAT GGA  576
Met Asp Gly Leu Arg Lys Arg Asn Thr Lys Lys Val Lys Lys Asn Gly
            180                 185                 190

GTT AAA GTC CGC TTT TTA TCT GAA GAA GAG TTA CCT ATA TTT AGG TCA  624
Val Lys Val Arg Phe Leu Ser Glu Glu Glu Leu Pro Ile Phe Arg Ser
        195                 200                 205

TTT ATG GAG GAT ACC TCT GAA ACT AAA GAT TTT GCA GAT AGA GAA GAT  672
Phe Met Glu Asp Thr Ser Glu Thr Lys Asp Phe Ala Asp Arg Glu Asp
    210                 215                 220

AGT TTT TAT TAC AAC AGA TTC AAA CAT TAT AAA GAC CGT GTT TTA GTA  720
Ser Phe Tyr Tyr Asn Arg Phe Lys His Tyr Lys Asp Arg Val Leu Val
225                 230                 235                 240
```

```
CCA CTA GCC TAT ATT AAC TTT GAT GAG TAT ATA GAG GAA CTA AAT AAT  768
Pro Leu Ala Tyr Ile Asn Phe Asp Glu Tyr Ile Glu Glu Leu Asn Asn
            245                 250             255

GAA AGA AAT GTG CTT AAT AAA GAT TAT AAT AAA GCT TTA AAA GAC ATT  816
Glu Arg Asn Val Leu Asn Lys Asp Tyr Asn Lys Ala Leu Lys Asp Ile
            260                 265             270

GAG AAA CGT CCA GAG AAT AAA AAA GCA CAT AAC AAA AAG GAA AAT TTA  864
Glu Lys Arg Pro Glu Asn Lys Lys Ala His Asn Lys Lys Glu Asn Leu
            275                 280             285

GAA CAA CAA CTC GAT GCA AAT CAG CAA AAA ATT AAT GAA GCT AAA AAC  912
Glu Gln Gln Leu Asp Ala Asn Gln Gln Lys Ile Asn Glu Ala Lys Asn
            290                 295             300

TTA AAA CAA GAA CAT GGC AAT GAA TTA CCC ATC TCT GCT GGC TTC TTT  960
Leu Lys Gln Glu His Gly Asn Glu Leu Pro Ile Ser Ala Gly Phe Phe
305             310                 315             320

ATA ATT AAT CCG TTT GAA GTA GTT TAC TAC GCT GGT GGA ACT TCA AAT 1008
Ile Ile Asn Pro Phe Glu Val Val Tyr Tyr Ala Gly Gly Thr Ser Asn
            325                 330             335

CGT TAT CGC CAT TTT GCA GGG AGC TAT GCG GTT CAA TGG AAG ATG ATT 1056
Arg Tyr Arg His Phe Ala Gly Ser Tyr Ala Val Gln Trp Lys Met Ile
            340                 345             350

AAC TAT GCA ATT GAA CAT GGT ATT AAT CGG TAT AAT TTC TAT GGT ATT 1104
Asn Tyr Ala Ile Glu His Gly Ile Asn Arg Tyr Asn Phe Tyr Gly Ile
            355                 360             365

AGT GGT GAC TTT AGT GAA GAT GCT GAA GAT GCT GGC GTA GTT AAG TTT 1152
Ser Gly Asp Phe Ser Glu Asp Ala Glu Asp Ala Gly Val Val Lys Phe
        370                 375             380

AAA AAG GGC TAT GAT GCC GAT GTT ATA GAA TAC GTT GGT GAC TTT ATT 1200
Lys Lys Gly Tyr Asp Ala Asp Val Ile Glu Tyr Val Gly Asp Phe Ile
385             390                 395             400

AAA CCT ATT AAT AAA CCA ATG TAT AAC ATT TAT AGA ACA CTT AAA AAA 1248
Lys Pro Ile Asn Lys Pro Met Tyr Asn Ile Tyr Arg Thr Leu Lys Lys
            405                 410             415

CTA AAG AAA                                                      1257
Leu Lys Lys
```

The synthesis of the FemA protein of the present invention may proceed by solid phase peptide synthesis or by recombinant methods. Both methods are described in U.S. Pat. No. 4,617,149, the entire teaching of which is herein incorporated by reference. Recombinant methods are preferred if a high yield is desired. The principles of solid phase chemical synthesis of polypeptides are well known in the art and may be found in general texts in the area such as Dugas, H. and Penney, C., *Bioorganic Chemistry* (1981), Springer-Verlag, New York, pgs. 54–92.

Figure 1:
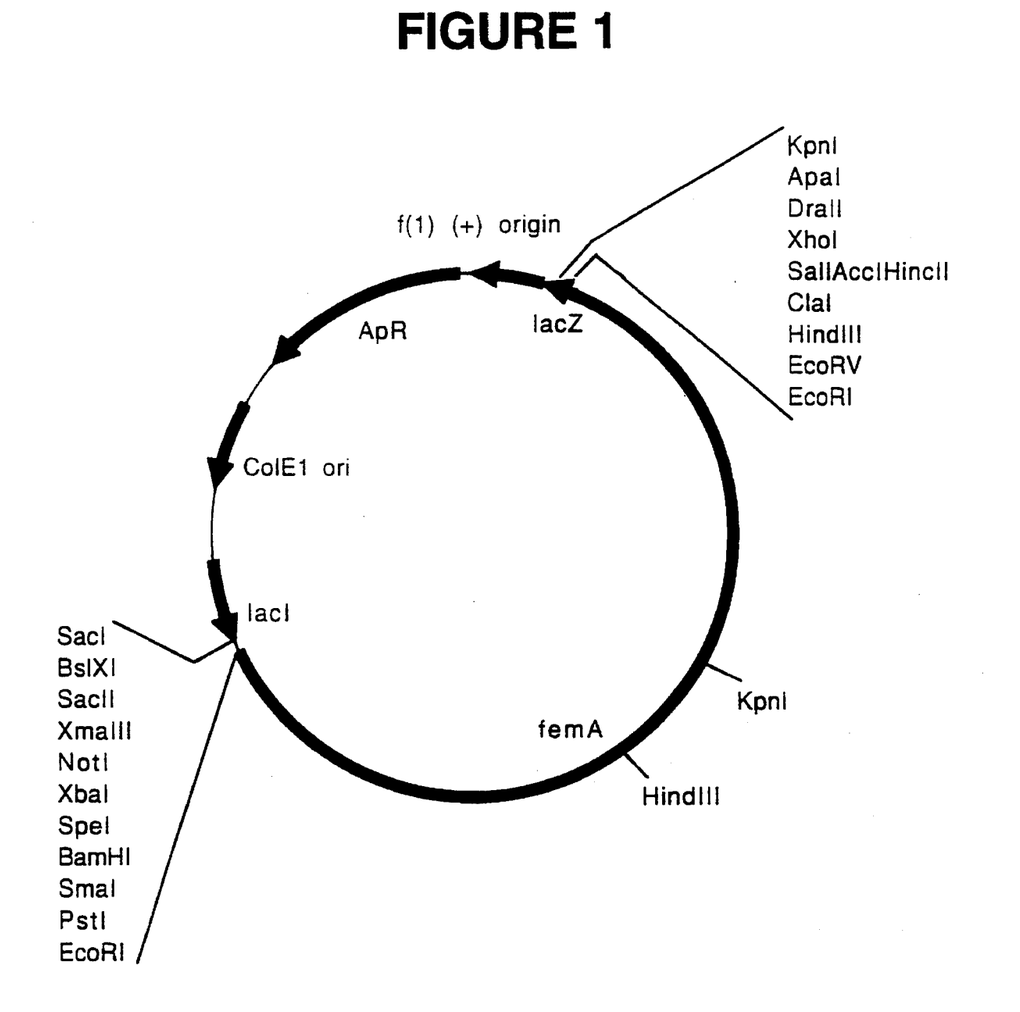
FIG. 1—A restriction site and function map of plasmid pPSJ180.

Synthesis of the FemA protein can be achieved by recombinant DNA technology. Synthetic genes, the in vitro or in vivo transcription and translation of which will result in the production of the FemA protein may be constructed by techniques well known in the art. Owing to the natural degeneracy of the genetic code, the skilled artisan will recognize that a sizable yet definite number of DNA sequences may be constructed which encode the FemA protein. All such genes are provided by the present invention. A preferred gene encoding the FemA protein is the natural femA gene of *Staphylococcus epidermidis*, which is SEQ ID NO: 1. This preferred femA gene is available on an ~3.7 kb EcoRI restriction fragment of plasmid pPSJ180, publicly available and on deposit in *Escherichia coli* DH5α at the National Center for Agricultural Utilization Research, 1815 North University Street, Peoria, Ill. 61604-39999, under accession number NRRL B-21024 (date of deposit: Dec. 8, 1992). A restriction site and function map of pPSJ180 is provided in FIG. 1 of the drawings.

The femA gene may be created by synthetic methodology. Such methodology of synthetic gene construction is well known in the art. See Brown et al. (1979) *Methods in Enzymology*, Academic Press, N.Y., 68:109–151. The femA DNA sequence may be generated using a conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

To effect the translation of the FemA protein, one inserts the engineered synthetic DNA sequence in any of a large number of appropriate recombinant DNA expression vectors through the use of appropriate restriction endonucleases and DNA ligase. The synthetic femA gene should be designed to possess restriction endonuclease cleavage sites at either end of the transcript to facilitate isolation from and integration into these amplification and expression plasmids. The particular endonucleases employed will be dictated by the restriction endonuclease cleavage pattern of the parent expression vector to be employed. The choice of restriction sites are chosen so as to properly orient the FemA coding sequence with control sequences to achieve proper in-frame reading and expression of the FemA molecule. The FemA coding sequence must be positioned so as to be in proper reading frame with the promoter and ribosome binding site of the expression vector, both of which are functional in the host cell in which the FemA protein is to be expressed. The FemA protein may be expressed in any number of well-known eucaryotic or procaryotic hosts using known promoters and vectors. Some of the potential hosts, in addition to *E. coli*, include the yeasts *Saccharomyces cerevisiae* and *Pichia pastoris*, Bacillus, and cells infected with baculovirus.

To achieve efficient transcription of the synthetic gene, said gene must be operably associated with a promoter operator region. In one practice of the invention, the promoter-operator region of the synthetic gene encoding SEQ ID NO: 2 is placed in the same sequential orientation with respect to the ATG start codon of the synthetic gene as the promoter-operator occupies with respect to the ATG-start codon of the gene from which it was derived. Synthetic or modified promoter operator regions have been created and are well known in the art. When employing such synthetic or modified promoter-operator regions they should be oriented with respect to the ATG-start codon of the femA gene as directed by their creators. In one practice of the invention as exemplified herein, where the host cell is an *E. Coli* host cell, said promoter-operator region is the phage T7 promoter-operator region.

Figure 2:
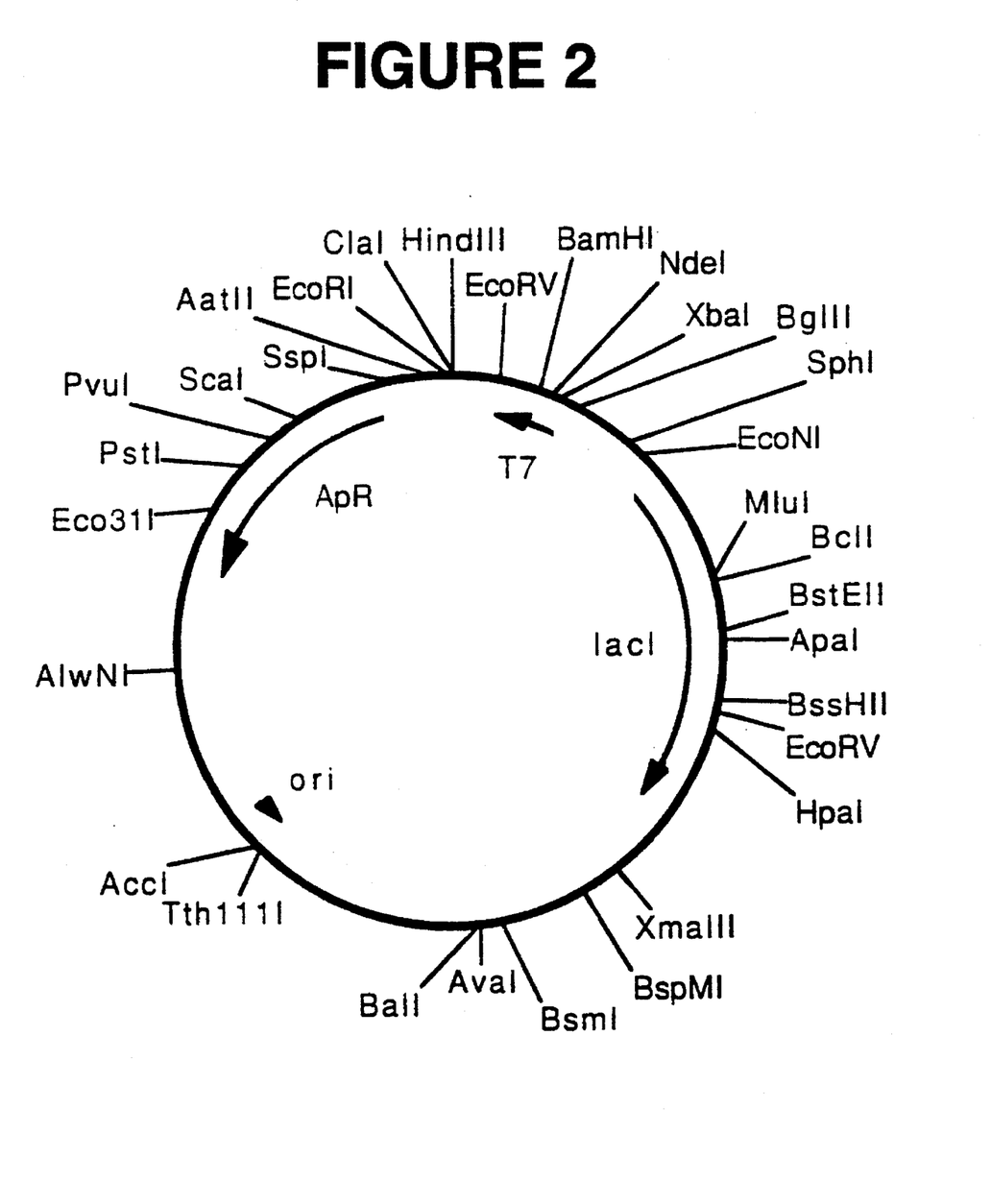
FIG. 2—A restriction site and function map of plasmid pET-11A.

A variety of expression vectors useful for transforming procaryotic cells are well known in the art. A preferred vector for expression in an *E. coli* host cell is derived from *E. coli* plasmid pET-11A, which comprises the phage T7 promoter. A restriction site and function map of pET-11A appears in FIG. 2 of the accompanying drawings. Plasmid pET-11A is publicly available from Novagen, Inc. (565 Science Drive, Madison, Wis. 53711) under catalog #69436-1. The preferred host strain is *E. coli* BL21(DE3), also available from Novagen under catalog #69387-1.

The techniques of transforming cells with the aforementioned vectors are well known in the art and may be found in such general references as Sambrook et al., *Molecular Cloning: A Laboratory Manual* (1988), Cold Spring Harbor Laboratory Press, Cold Spring Harbor, N.Y. or Ausubel et al., *Current Protocols in Molecular Biology* (1989), John Wiley & Sons, New York, N.Y. and supplements. The techniques involved in the transformation of *E. coli* cells used in the preferred practice of the invention as exemplified herein are well known in the art. The precise conditions under which the transformed *E. coli* cells are cultured is dependent on the nature of the *E. coli* host cell line and the expression or cloning vectors employed. For example, vectors which incorporate thermoinducible promoter-operator regions, such as the cI857 thermoinducible lambda-phage promoter-operator region, require a temperature shift from about 30° to about 40° C. in the culture conditions so as to induce protein synthesis.

In a preferred embodiment of the invention *E. coli* K12 BL21 (DE3) cells were employed as host cells but numerous other cell lines are available. The transformed host cells are then plated on appropriate media under the selective pressure of the antibiotic corresponding to the resistance gene present on the expression plasmid. The cultures are then incubated for a time and temperature appropriate to the host cell line employed. Specifically, with *E. coli* K12 BL21 (DE3) cells, the femA gene is placed under the control of a promoter transcribed specifically by the T7 RNA polymerase. Induction of transcription of the femA gene is accomplished by the addition of isopropylthiogalactoside (IPTG) to the growth medium, which induces expression of the T7 RNA polymerase gene under the control of the lacUV5 promoter. The T7 RNA polymerase is then available to transcribe the femA gene.

General techniques of protein purification are well-known to those of ordinary skill in the art. See Creighton, T. E., *Protein Structure: A Practical Approach* (1989), IRL Press, Oxford, England and Bollag, D. M. and Edelstein, S. J., *Protein Methods* (1991), Wiley-Liss, New York, N.Y. Proteins which are expressed in high-level bacterial expression systems characteristically aggregate in granules or inclusion bodies which contain high levels of the overexpressed protein. Kreuger et al. (1990) in *Protein Folding*, Gierasch and King, eds., pgs 136–142, American Association for the Advancement of Science Publication No. 89-18S, Washington, D.C. and Sambrook et al., *Molecular Cloning: A Laboratory Manual* (1988), pp. 17.37–17.41, Cold Spring Harbor Laboratory Press, Cold Spring Harbor, N.Y. The FemA protein sometimes aggregates into inclusion bodies when expressed under the control of phage T7 promoter. Such protein aggregates must be solubilized to provide further purification and isolation of the desired protein product. A variety of techniques using strongly denaturing solutions such as guanidinium-HCl and/or weakly denaturing solutions such as dithiothreitol (DTT) are used to solubilize the proteins.

Recombinantly produced proteins may be purified by a variety of techniques well known in the art such as ion exchange chromatography, size exclusion chromatography, electrophoresis, differential centrifugation, reversed phase high performance liquid chromatography, immunoaffinity chromatography, and the like. Protocols for use of these individual techniques or combinations thereof are well known in the art. Gradual removal of the denaturing agents (often by dialysis) in a refolding solution allows the denatured protein to assume its native conformation. The particular conditions for denaturation and refolding are determined by the particular protein expression system and/or protein in question. The S-sulfonates of the peptide molecules are converted to the disulfide paired, folded FemA molecules using a combination of high pH and added thiol in substantial accordance with the teaching of Frank, B. H. et al., (1981) in *Peptides. Synthesis, Structure and Function. Proceedings of the Seventh American Peptide Symposium* (Rich, D. H. and Gross, E., eds.) pp. 729–738, Pierce Chemical Co., Rockford, Ill.

The femA gene may be used in gene disruption studies in *Staphylococcus epidermidis*. Although it is believed that the FemA protein is involved in the formation of a pentaglycine bridge in the cell wall of the bacterium, gene disruption will allow one to ascertain the precise effect of the loss of the femA gene. Gene disruption experiments in *Staphytococcus aureus* have revealed that a loss of femA results in an ~40% reduction in cell wall glycine content. A similar result might be anticipated for *S. epidermidis*. Once determined, this information can be used to generate an assay for agents which inhibit the FemA protein, and are therefore useful in combination with antibiotics to treat methicillin-resistant bacteria.

The FemA protein of SEQ ID NO: 2 may be produced by recombinant methods. Recombinant methods are preferred if a high yield is desired. The present invention thus comprises a method for constructing a recombinant host cell capable of expressing SEQ ID NO: 2, said method comprising transforming a host cell with a recombinant DNA vector that comprises an isolated DNA sequence of claim 1. The present invention also comprises a method for expressing SEQ ID NO: 2 in a recombinant host cell; said method comprising culturing said transformed host cell of claim 5 under conditions suitable for gene expression.

The following Examples are provided to further illustrate and exemplify, but not limit the scope of, the invention.

EXAMPLE 1

Source of the *Staphylococcus epidermidis* femA
Gene ps Isolation of Plasmid pPSJ180

A lyophil of *E. coli* K12 DH5α/pPSJ180 can be obtained from the Northern Regional Research Laboratories (NRRL), Peoria, Ill. 61604, under the accession number NRRL B-21024 (date of deposit: Dec. 8, 1992). The pPSJ180 plasmid may be isolated from *E. coli* K12 DH5α/pPSJ180 using techniques well-known to those skilled in the art. See Sambrook et al., *Molecular Cloning: A Laboratory Manual* (1988), Cold Spring Harbor Laboratory Press, Cold Spring Harbor, N.Y. or Ausubel et al., *Current Protocols in Molecular Biology* (1989), John Wiley & Sons, New York, N.Y. and supplements.

Isolation of the *Staphylococcus epidermidis* femA gene via the polymerase chain reaction Isolated plasmid pPSJ180 is used as the template for the polymerase chain reaction at a concentration of 10 ng/reaction. Vent$_R$™ DNA polymerase (2 units/μl, Catalog #254, New England Biolabs, 32 Tozer Road, Beverly, Mass. 01915-9965) is used with standard Vent$_R$™ DNA polymerase buffer (1X=10 mM KCl, 20 mM Tris-HCl (pH 8.8 at 25° C.), 10 mM (NH$_4$)$_2$SO$_4$, 2 mM MgSO$_4$, 0.1% Triton X-100). The PCR primers used are AGATATAAAGATCTA-GATGGGAGTTATGAA (SEQ ID NO: 3) and ATTTCAT-AATTAGATGGATCCCTTCTTAAAATC (SEQ ID NO: 4). The reaction is carried out by 3 cycles of 94° C. for 15 seconds, 40° C. for 15 seconds and 72° C. for 1 minute followed by 20 cycles of 94° C. for 15 seconds, 55° C. for 15 seconds and 72° C. for 1 minute.

The reaction is transferred to a Centricon 100 microconcentrator (Amicon, Inc., 72 Cherry Hill, Beverly, Mass. 01915) and washed with 1 ml of water. The microconcentrator is then subjected to centrifugation at 3000 rpm in a microcentrifuge for 30 minutes. The reaction is then diluted to 200 μl (from ~50 μl) with 1X XbaI restriction enzyme buffer. To this is added 50 units of XbaI and 50 units of BamHI. The DNA is then digested for 90 minutes at 37° C. The DNA is phenol extracted and ethanol precipitated.

EXAMPLE 2

Construction of an Expression Plasmid Containing the femA Gene

The DNA created in Example 1 is then ligated to the 5.6 kb XbaI-BamHI fragment of pET-11A (available from Novagen, Inc. (565 Science Drive, Madison, Wis. 53711) under catalog #69436-1. This plasmid is then transformed into *E. coli* BL21 (DE3) (also available from Novagen, Inc. under catalog #69387-1) using techniques well known to those of ordinary skill in the art.

EXAMPLE 3

Expression of the FemA Protein

*E. coli* BL21 (DE3) transformed with the femA expression plasmid are grown overnight in TY broth (per liter 10 g tryptone, 5 g yeast extract and 5 g NaCl) and 100 μg/ml ampicillin. The cells are then diluted 1/50 into TY broth+ampicillin and grown at 37° C. for 60 minutes. Expression is induced by adding isropylthiogalactoside (IPTG) to 0.4 mM. Samples are taken at 0 and 6 hours and run on a % SDS-polyacrylamide gel using techniques described in Sambrook et al., *Molecular Cloning: A Laboratory Manual* (1988), pp. 18.47–18.59, Cold Spring Harbor Laboratory Press, Cold Spring Harbor, N.Y. An induced protein band is visible by staining with Coomassie Blue at the predicted size of 49,000 daltons.

---

We claim:

1. A DNA compound that comprises an isolated DNA sequence which is SEQ ID NO:1.

2. A recombinant DNA vector that comprises an isolated DNA sequence of SEQ ID NO: 1.

3. A recombinant DNA vector of claim 2 that further comprises a promoter positioned to drive expression of said isolated DNA sequence.

4. A method for expressing SEQ ID NO: 2 in a recombinant host cell; said method comprising culturing a recombinant host cell transformed with a recombinant DNA vector that comprises an isolated DNA sequence of SEQ ID NO: 1.

5. A recombinant host cell transformed with a recombinant DNA vector of claim 2.

\* \* \* \* \*

UNITED STATES PATENT AND TRADEMARK OFFICE
CERTIFICATE OF CORRECTION

PATENT NO. : 5,587,307                     Page 1 of 5
DATED     : December 24, 1996
INVENTOR(S) : William E. Alborn, Jr. et al It is certified that error appears in the above-indentified patent and that said Letters Patent is hereby corrected as shown below:

ABSTRACT, line 1 reads ..."femA"... should read --*femA*--

ABSTRACT, line 3 reads ..."femA"... should read --*femA*--

Column 1, line 16 reads ..."mecA"... should read --*mecA*--

Column 1, line 27 reads ..."mecA"... should read --*mecA*--

Column 1, line 28 reads ..."mecA"... should read --*mecA*--

Column 1, line 30 reads ..."mecA"... should read --*mecA*--

Column 2, line 5 reads ..."mecA"... should read --*mecA*--

Column 2, line 15 reads ..."(fem)."... should read --*(fem)*.--

Column 2, line 16 reads ..."mecA"... should read --*mecA*--

UNITED STATES PATENT AND TRADEMARK OFFICE
CERTIFICATE OF CORRECTION

PATENT NO. : 5,587,307
DATED : December 24, 1996
INVENTOR(S) : William E. Alborn, Jr. et al It is certified that error appears in the above-indentified patent and that said Letters Patent is hereby corrected as shown below:

Column 2, line 19 reads ..."femA"... should read --*femA*--

Column 2, line 20 reads ..."femB"... should read --*femB*--

Column 2, line 28 reads ..."mecA"... should read --*mecA*--

Column 2, line 34 reads ..."femA"... should read --*femA*--

Column 2, line 39 reads ..."femA"... should read --*femA*--

Column 3, line 42 reads ..."femA"... should read --*femA*--

Column 7, line 9 reads ..."herein, The"... should read --herein. The--

Column 8, line 8 reads ..."femA"... should read --*femA*--

UNITED STATES PATENT AND TRADEMARK OFFICE
CERTIFICATE OF CORRECTION

PATENT NO. : 5,587,307
DATED : December 24, 1996
INVENTOR(S) : William E. Alborn, Jr. et al Page 3 of 5

It is certified that error appears in the above-indentified patent and that said Letters Patent is hereby corrected as shown below:

Column 8, line 10 reads ..."femA"... should read --*femA*--

Column 9, line 15 reads ..."femA"... should read --*femA*--

Column 11, line 50-51 reads ..."in vitro or in vivo"... should read --*in vitro or in vivo*--

Column 11, line 59 reads ..."femA"... should read --*femA*--

Column 11, line 60 reads ..."femA"... should read --*femA*--

Column 12, line 39 reads ..."femA"... should read --*femA*--

Column 12, line 41 reads ..."See"... should read --*See*--

Column 12, line 42 reads ..."femA"... should read --*femA*--

Column 12, line 52 reads ..."femA"... should read --*femA*--

Column 13, line 16 reads ..."femA"... should read --*femA*--

Column 13, line 57 reads ..."femA"... should read --*femA*--

UNITED STATES PATENT AND TRADEMARK OFFICE
CERTIFICATE OF CORRECTION

PATENT NO. : 5,587,307
DATED : December 24, 1996
INVENTOR(S) : William E. Alborn, Jr. et al It is certified that error appears in the above-indentified patent and that said Letters Patent is hereby corrected as shown below:

Column 13, line 59 reads ..."femA"... should read --*femA*--

Column 13, line 63 reads ..."lacUV5"... should read --*lacUV5*--

Column 13, line 64 reads ..."femA"... should read --*femA*--

Column 13, line 66 reads ..."See"... should read --*See*--

Column 14, line 42 reads ..."femA"... should read --*femA*--

Column 14, line 47 reads ..."femA"... should read --*femA*--

Column 14, line 48 reads ..."femA"... should read --*femA*--

Column 15, line 3 reads ..."femA"... should read --*femA*--

Column 15, line 10 reads ..."See"... should read --*See*--

UNITED STATES PATENT AND TRADEMARK OFFICE
CERTIFICATE OF CORRECTION

PATENT NO. : 5,587,307
DATED : December 24, 1996
INVENTOR(S) : William E. Alborn, Jr. et al It is certified that error appears in the above-indentified patent and that said Letters Patent is hereby corrected as shown below:

Column 15, line 16-17 reads ..."Isolation of the *Staphylococcus epidermidis* femA gene via the polymerase chain reaction"...
should read-(Centered as a Title)
   Isolation of the *Staphylococcus epidermidis femA* gene via the polymerase chain reaction--

Column 16, line 10 reads ..."femA"... should read --*femA*--

Column 16, line 23 reads ..."femA"... should read --*femA*--

Signed and Sealed this

Fourteenth Day of October, 1997

Attest:

BRUCE LEHMAN

*Attesting Officer*    Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1257 base pairs
        ( B ) TYPE: nucleic acid
        ( C ) STRANDEDNESS: double
        ( D ) TOPOLOGY: linear     ( i i ) MOLECULE TYPE: DNA (genomic)

( i x ) FEATURE:
        ( A ) NAME/KEY: CDS
        ( B ) LOCATION: 1..1257

( x i ) SEQUENCE DESCRIPTION: SEQ ID NO:1:

```
ATG  AAG  ATG  AAG  TTT  ACG  AAT  TTG  ACA  GCT  AAA  GAA  TTT  AGT  GAC  TTT       48
Met  Lys  Met  Lys  Phe  Thr  Asn  Leu  Thr  Ala  Lys  Glu  Phe  Ser  Asp  Phe
 1             5                        10                       15

ACT  GAT  CGT  ATG  ACA  TAT  AGT  CAT  TTT  ACA  CAA  ATG  GAA  GGT  AAT  TAC       96
Thr  Asp  Arg  Met  Thr  Tyr  Ser  His  Phe  Thr  Gln  Met  Glu  Gly  Asn  Tyr
                   20                       25                       30

GAA  TTA  AAG  GTT  GCT  GAA  GGT  ACC  GAG  TCA  CAT  TTA  GTT  GGA  ATT  AAA      144
Glu  Leu  Lys  Val  Ala  Glu  Gly  Thr  Glu  Ser  His  Leu  Val  Gly  Ile  Lys
            35                       40                       45
```

| | | | | | | | | | | | | | | | | |
|---|---|---|---|---|---|---|---|---|---|---|---|---|---|---|---|---|
| AAT | AAT | GAT | AAC | GAA | GTG | ATT | GCA | GCT | TGT | TTA | TTA | ACA | GCT | GTT | CCT | 192 |
| Asn | Asn | Asp | Asn | Glu | Val | Ile | Ala | Ala | Cys | Leu | Leu | Thr | Ala | Val | Pro | |
| | 50 | | | | 55 | | | | | 60 | | | | | | |
| GTA | ATG | AAA | ATA | TTT | AAA | TAT | TTT | TAT | TCC | AAT | CGC | GGT | CCA | GTA | ATA | 240 |
| Val | Met | Lys | Ile | Phe | Lys | Tyr | Phe | Tyr | Ser | Asn | Arg | Gly | Pro | Val | Ile | |
| 65 | | | | | 70 | | | | | 75 | | | | | 80 | |
| GAT | TAT | AAT | AAT | AAA | GAG | CTT | GTA | CAT | TTT | TTC | TTT | AAT | GAA | TTG | AGT | 288 |
| Asp | Tyr | Asn | Asn | Lys | Glu | Leu | Val | His | Phe | Phe | Phe | Asn | Glu | Leu | Ser | |
| | | | | 85 | | | | | 90 | | | | | 95 | | |
| AAA | TAT | GTA | AAA | AAA | TAT | AAT | TGT | TTA | TAT | TTA | AGA | GTT | GAC | CCA | TAC | 336 |
| Lys | Tyr | Val | Lys | Lys | Tyr | Asn | Cys | Leu | Tyr | Leu | Arg | Val | Asp | Pro | Tyr | |
| | | | 100 | | | | | 105 | | | | | 110 | | | |
| CTT | CCA | TAT | CAA | TAT | TTA | AAT | CAT | GAG | GGA | GAA | ATA | ACT | GGA | AAT | GCA | 384 |
| Leu | Pro | Tyr | Gln | Tyr | Leu | Asn | His | Glu | Gly | Glu | Ile | Thr | Gly | Asn | Ala | |
| | | 115 | | | | | 120 | | | | | 125 | | | | |
| GGT | CAT | GAT | TGG | ATT | TTT | GAT | GAA | TTA | GAG | AGT | TTA | GGA | TAT | AAA | CAC | 432 |
| Gly | His | Asp | Trp | Ile | Phe | Asp | Glu | Leu | Glu | Ser | Leu | Gly | Tyr | Lys | His | |
| | 130 | | | | | 135 | | | | | 140 | | | | | |
| GAA | GGA | TTC | CAC | AAA | GGA | TTT | GAT | CCT | GTA | TTA | CAA | ATC | CGA | TAT | CAT | 480 |
| Glu | Gly | Phe | His | Lys | Gly | Phe | Asp | Pro | Val | Leu | Gln | Ile | Arg | Tyr | His | |
| 145 | | | | | 150 | | | | | 155 | | | | | 160 | |
| TCT | GTT | CTA | AAT | TTA | GCA | AAC | AAA | AGT | GCT | AAT | GAT | GTT | TTA | AAA | AAC | 528 |
| Ser | Val | Leu | Asn | Leu | Ala | Asn | Lys | Ser | Ala | Asn | Asp | Val | Leu | Lys | Asn | |
| | | | | 165 | | | | | 170 | | | | | 175 | | |
| ATG | GAT | GGT | TTA | AGA | AAG | CGT | AAT | ACT | AAA | AAA | GTT | AAG | AAA | AAT | GGA | 576 |
| Met | Asp | Gly | Leu | Arg | Lys | Arg | Asn | Thr | Lys | Lys | Val | Lys | Lys | Asn | Gly | |
| | | | 180 | | | | | 185 | | | | | 190 | | | |
| GTT | AAA | GTC | CGC | TTT | TTA | TCT | GAA | GAA | GAG | TTA | CCT | ATA | TTT | AGG | TCA | 624 |
| Val | Lys | Val | Arg | Phe | Leu | Ser | Glu | Glu | Glu | Leu | Pro | Ile | Phe | Arg | Ser | |
| | | 195 | | | | | 200 | | | | | 205 | | | | |
| TTT | ATG | GAG | GAT | ACC | TCT | GAA | ACT | AAA | GAT | TTT | GCA | GAT | AGA | GAA | GAT | 672 |
| Phe | Met | Glu | Asp | Thr | Ser | Glu | Thr | Lys | Asp | Phe | Ala | Asp | Arg | Glu | Asp | |
| | 210 | | | | | 215 | | | | | 220 | | | | | |
| AGT | TTT | TAT | TAC | AAC | AGA | TTC | AAA | CAT | TAT | AAA | GAC | CGT | GTT | TTA | GTA | 720 |
| Ser | Phe | Tyr | Tyr | Asn | Arg | Phe | Lys | His | Tyr | Lys | Asp | Arg | Val | Leu | Val | |
| 225 | | | | | 230 | | | | | 235 | | | | | 240 | |
| CCA | CTA | GCC | TAT | ATT | AAC | TTT | GAT | GAG | TAT | ATA | GAG | GAA | CTA | AAT | AAT | 768 |
| Pro | Leu | Ala | Tyr | Ile | Asn | Phe | Asp | Glu | Tyr | Ile | Glu | Glu | Leu | Asn | Asn | |
| | | | | 245 | | | | | 250 | | | | | 255 | | |
| GAA | AGA | AAT | GTG | CTT | AAT | AAA | GAT | TAT | AAT | AAA | GCT | TTA | AAA | GAC | ATT | 816 |
| Glu | Arg | Asn | Val | Leu | Asn | Lys | Asp | Tyr | Asn | Lys | Ala | Leu | Lys | Asp | Ile | |
| | | | 260 | | | | | 265 | | | | | 270 | | | |
| GAG | AAA | CGT | CCA | GAG | AAT | AAA | AAA | GCA | CAT | AAC | AAA | AAG | GAA | AAT | TTA | 864 |
| Glu | Lys | Arg | Pro | Glu | Asn | Lys | Lys | Ala | His | Asn | Lys | Lys | Glu | Asn | Leu | |
| | | 275 | | | | | 280 | | | | | 285 | | | | |
| GAA | CAA | CAA | CTC | GAT | GCA | AAT | CAG | CAA | AAA | ATT | AAT | GAA | GCT | AAA | AAC | 912 |
| Glu | Gln | Gln | Leu | Asp | Ala | Asn | Gln | Gln | Lys | Ile | Asn | Glu | Ala | Lys | Asn | |
| | 290 | | | | | 295 | | | | | 300 | | | | | |
| TTA | AAA | CAA | GAA | CAT | GGC | AAT | GAA | TTA | CCC | ATC | TCT | GCT | GGC | TTC | TTT | 960 |
| Leu | Lys | Gln | Glu | His | Gly | Asn | Glu | Leu | Pro | Ile | Ser | Ala | Gly | Phe | Phe | |
| 305 | | | | | 310 | | | | | 315 | | | | | 320 | |
| ATA | ATT | AAT | CCG | TTT | GAA | GTA | GTT | TAC | TAC | GCT | GGT | GGA | ACT | TCA | AAT | 1008 |
| Ile | Ile | Asn | Pro | Phe | Glu | Val | Val | Tyr | Tyr | Ala | Gly | Gly | Thr | Ser | Asn | |
| | | | | 325 | | | | | 330 | | | | | 335 | | |
| CGT | TAT | CGC | CAT | TTT | GCA | GGG | AGC | TAT | GCG | GTT | CAA | TGG | AAG | ATG | ATT | 1056 |
| Arg | Tyr | Arg | His | Phe | Ala | Gly | Ser | Tyr | Ala | Val | Gln | Trp | Lys | Met | Ile | |
| | | | 340 | | | | | 345 | | | | | 350 | | | |
| AAC | TAT | GCA | ATT | GAA | CAT | GGT | ATT | AAT | CGG | TAT | AAT | TTC | TAT | GGT | ATT | 1104 |
| Asn | Tyr | Ala | Ile | Glu | His | Gly | Ile | Asn | Arg | Tyr | Asn | Phe | Tyr | Gly | Ile | |
| | | 355 | | | | | 360 | | | | | 365 | | | | |

| | | | | | | | | | | | | | | | | |
|---|---|---|---|---|---|---|---|---|---|---|---|---|---|---|---|---|
| AGT | GGT | GAC | TTT | AGT | GAA | GAT | GCT | GAA | GAT | GCT | GGC | GTA | GTT | AAG | TTT | 1152 |
| Ser | Gly | Asp | Phe | Ser | Glu | Asp | Ala | Glu | Asp | Ala | Gly | Val | Val | Lys | Phe | |
| | 370 | | | | 375 | | | | | 380 | | | | | | |
| AAA | AAG | GGC | TAT | GAT | GCC | GAT | GTT | ATA | GAA | TAC | GTT | GGT | GAC | TTT | ATT | 1200 |
| Lys | Lys | Gly | Tyr | Asp | Ala | Asp | Val | Ile | Glu | Tyr | Val | Gly | Asp | Phe | Ile | |
| 385 | | | | | 390 | | | | | 395 | | | | | 400 | |
| AAA | CCT | ATT | AAT | AAA | CCA | ATG | TAT | AAC | ATT | TAT | AGA | ACA | CTT | AAA | AAA | 1248 |
| Lys | Pro | Ile | Asn | Lys | Pro | Met | Tyr | Asn | Ile | Tyr | Arg | Thr | Leu | Lys | Lys | |
| | | | | 405 | | | | | 410 | | | | | 415 | | |
| CTA | AAG | AAA | | | | | | | | | | | | | | 1257 |
| Leu | Lys | Lys | | | | | | | | | | | | | | |

( 2 ) INFORMATION FOR SEQ ID NO:2:

( i ) SEQUENCE CHARACTERISTICS:
        ( A ) LENGTH: 419 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

| | | | | | | | | | | | | | | |
|---|---|---|---|---|---|---|---|---|---|---|---|---|---|---|
| Met | Lys | Met | Lys | Phe | Thr | Asn | Leu | Thr | Ala | Lys | Glu | Phe | Ser | Asp | Phe |
| 1 | | | | 5 | | | | | 10 | | | | | 15 |
| Thr | Asp | Arg | Met | Thr | Tyr | Ser | His | Phe | Thr | Gln | Met | Glu | Gly | Asn | Tyr |
| | | | 20 | | | | | 25 | | | | | 30 | |
| Glu | Leu | Lys | Val | Ala | Glu | Gly | Thr | Glu | Ser | His | Leu | Val | Gly | Ile | Lys |
| | | 35 | | | | | 40 | | | | | 45 | | |
| Asn | Asn | Asp | Asn | Glu | Val | Ile | Ala | Ala | Cys | Leu | Leu | Thr | Ala | Val | Pro |
| | 50 | | | | | 55 | | | | | 60 | | | |
| Val | Met | Lys | Ile | Phe | Lys | Tyr | Phe | Tyr | Ser | Asn | Arg | Gly | Pro | Val | Ile |
| 65 | | | | | 70 | | | | | 75 | | | | | 80 |
| Asp | Tyr | Asn | Asn | Lys | Glu | Leu | Val | His | Phe | Phe | Phe | Asn | Glu | Leu | Ser |
| | | | | 85 | | | | | 90 | | | | | 95 | |
| Lys | Tyr | Val | Lys | Lys | Tyr | Asn | Cys | Leu | Tyr | Leu | Arg | Val | Asp | Pro | Tyr |
| | | | 100 | | | | | 105 | | | | | 110 | | |
| Leu | Pro | Tyr | Gln | Tyr | Leu | Asn | His | Glu | Gly | Glu | Ile | Thr | Gly | Asn | Ala |
| | | 115 | | | | | 120 | | | | | 125 | | | |
| Gly | His | Asp | Trp | Ile | Phe | Asp | Glu | Leu | Glu | Ser | Leu | Gly | Tyr | Lys | His |
| | 130 | | | | | 135 | | | | | 140 | | | | |
| Glu | Gly | Phe | His | Lys | Gly | Phe | Asp | Pro | Val | Leu | Gln | Ile | Arg | Tyr | His |
| 145 | | | | | 150 | | | | | 155 | | | | | 160 |
| Ser | Val | Leu | Asn | Leu | Ala | Asn | Lys | Ser | Ala | Asn | Asp | Val | Leu | Lys | Asn |
| | | | | 165 | | | | | 170 | | | | | 175 | |
| Met | Asp | Gly | Leu | Arg | Lys | Arg | Asn | Thr | Lys | Lys | Val | Lys | Lys | Asn | Gly |
| | | | 180 | | | | | 185 | | | | | 190 | | |
| Val | Lys | Val | Arg | Phe | Leu | Ser | Glu | Glu | Glu | Leu | Pro | Ile | Phe | Arg | Ser |
| | | 195 | | | | | 200 | | | | | 205 | | | |
| Phe | Met | Glu | Asp | Thr | Ser | Glu | Thr | Lys | Asp | Phe | Ala | Asp | Arg | Glu | Asp |
| | 210 | | | | | 215 | | | | | 220 | | | | |
| Ser | Phe | Tyr | Tyr | Asn | Arg | Phe | Lys | His | Tyr | Lys | Asp | Arg | Val | Leu | Val |
| 225 | | | | | 230 | | | | | 235 | | | | | 240 |
| Pro | Leu | Ala | Tyr | Ile | Asn | Phe | Asp | Glu | Tyr | Ile | Glu | Glu | Leu | Asn | Asn |
| | | | | 245 | | | | | 250 | | | | | 255 | |
| Glu | Arg | Asn | Val | Leu | Asn | Lys | Asp | Tyr | Asn | Lys | Ala | Leu | Lys | Asp | Ile |
| | | | 260 | | | | | 265 | | | | | 270 | | |
| Glu | Lys | Arg | Pro | Glu | Asn | Lys | Lys | Ala | His | Asn | Lys | Lys | Glu | Asn | Leu |

|     |     |     |     |     | 275 |     |     |     |     | 280 |     |     |     |     | 285 |     |     |     |     |
|-----|-----|-----|-----|-----|-----|-----|-----|-----|-----|-----|-----|-----|-----|-----|-----|-----|-----|-----|-----|
| Glu | Gln | Gln | Leu | Asp | Ala | Asn | Gln | Gln | Lys | Ile | Asn | Glu | Ala | Lys | Asn |
|     | 290 |     |     |     |     | 295 |     |     |     |     | 300 |     |     |     |     |
| Leu | Lys | Gln | Glu | His | Gly | Asn | Glu | Leu | Pro | Ile | Ser | Ala | Gly | Phe | Phe |
| 305 |     |     |     |     | 310 |     |     |     |     | 315 |     |     |     |     | 320 |
| Ile | Ile | Asn | Pro | Phe | Glu | Val | Val | Tyr | Tyr | Ala | Gly | Gly | Thr | Ser | Asn |
|     |     |     |     | 325 |     |     |     |     | 330 |     |     |     |     | 335 |     |
| Arg | Tyr | Arg | His | Phe | Ala | Gly | Ser | Tyr | Ala | Val | Gln | Trp | Lys | Met | Ile |
|     |     |     | 340 |     |     |     |     | 345 |     |     |     |     | 350 |     |     |
| Asn | Tyr | Ala | Ile | Glu | His | Gly | Ile | Asn | Arg | Tyr | Asn | Phe | Tyr | Gly | Ile |
|     |     | 355 |     |     |     |     | 360 |     |     |     |     | 365 |     |     |     |
| Ser | Gly | Asp | Phe | Ser | Glu | Asp | Ala | Glu | Asp | Ala | Gly | Val | Val | Lys | Phe |
|     | 370 |     |     |     |     | 375 |     |     |     |     | 380 |     |     |     |     |
| Lys | Lys | Gly | Tyr | Asp | Ala | Asp | Val | Ile | Glu | Tyr | Val | Gly | Asp | Phe | Ile |
| 385 |     |     |     |     | 390 |     |     |     |     | 395 |     |     |     |     | 400 |
| Lys | Pro | Ile | Asn | Lys | Pro | Met | Tyr | Asn | Ile | Tyr | Arg | Thr | Leu | Lys | Lys |
|     |     |     |     | 405 |     |     |     |     | 410 |     |     |     |     | 415 |     |
| Leu | Lys | Lys |

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

AGATATAAAG ATCTAGATGG GAGTTATGAA      30

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

ATTTCATAAT TAGATGGATC CCTTCTTAAA ATC      33